(12) United States Patent
Sadygov et al.

(10) Patent No.: US 7,555,393 B2
(45) Date of Patent: Jun. 30, 2009

(54) EVALUATING THE PROBABILITY THAT MS/MS SPECTRAL DATA MATCHES CANDIDATE SEQUENCE DATA

(75) Inventors: Rovshan Goumbatoglu Sadygov, San Jose, CA (US); Andreas Huhmer, Mountain View, CA (US)

(73) Assignee: Thermo Finnigan LLC, San Jose, CA (US)

( * ) Notice: Subject to any disclaimer, the term of this patent is extended or adjusted under 35 U.S.C. 154(b) by 106 days.

(21) Appl. No.: 11/809,703

(22) Filed: Jun. 1, 2007

(65) Prior Publication Data
US 2008/0300795 A1 Dec. 4, 2008

(51) Int. Cl.
*G01N 33/48* (2006.01)
(52) U.S. Cl. ....................................................... 702/19
(58) Field of Classification Search .................... 702/22, 702/23, 25, 27, 28, 29, 31; 250/281, 282, 250/287, 288; 324/307, 316, 318; 73/23.37, 73/659
See application file for complete search history.

(56) References Cited

U.S. PATENT DOCUMENTS

| | | | |
|---|---|---|---|
| 5,538,897 | A | 7/1996 | Yates, III et al. |
| 6,017,693 | A | 1/2000 | Yates, III et al. |
| 6,446,010 | B1 | 9/2002 | Eriksson et al. |
| 6,582,965 | B1 | 6/2003 | Townsend et al. |
| 6,891,154 | B2 | 5/2005 | Zhu et al. |
| 6,963,807 | B2 | 11/2005 | Townsend et al. |

(Continued)

FOREIGN PATENT DOCUMENTS

WO    WO 02/101355 A3    12/2002

OTHER PUBLICATIONS

Craig et al., "Tandem: matching proteins with tandem mass spectra," Bioinformatics Applications Note, vol. 20 ( No. 9), p. 1466-1467, (2004).

(Continued)

*Primary Examiner*—Aditya Bhat
(74) *Attorney, Agent, or Firm*—Michael C. Staggs (57) ABSTRACT

In one aspect of the present invention a new database search methodology is provided that provides a probability that spectral data from a non-ergodic reaction via mass spectrometry matches a candidate sequence from a set of sequences in a database by random. The methodology comprises two parts. The first part pre-processes the spectral data and retains only the most relevant data for the database search. The second part comprises searching a database using the pre-processed spectrum to assign a probability or expectation that the spectrum matches a candidate sequence from a set of sequences in a database by random. The search methodology uses a new probability model, a compound distribution based on the number of product ion mass-to-charge ratios and the number of intensity values that are shared between the product ion spectral data and the sequence database, to accurately predict the probability of the peptide identification being a correct match, and not a random event.

20 Claims, 5 Drawing Sheets

U.S. PATENT DOCUMENTS

| | | | |
|---|---|---|---|
| 7,158,862 | B2 | 1/2007 | Liebler et al. |
| 7,279,679 | B2 * | 10/2007 | Old et al. ............ 250/282 |
| 2003/0060983 | A1 * | 3/2003 | Figeys ............ 702/28 |
| 2004/0044481 | A1 | 3/2004 | Halpern |
| 2005/0221500 | A1 | 10/2005 | Reid et al. |

OTHER PUBLICATIONS

Wan et al., "PepHMM: A Hidden Markov Model Based Scoring Function for Mass Spectrometry Database Search," RECOMB 2005, p. 342-356, (2005).

Colinge et al., "OLAV: Towards high-throughput tandem mass spectrometry data identification," Proteomics, p. 1454-1463, (2003).

Sadygov et al., "A Hypergeometric Probability Model for Protein Identification and Validation Using Tandem Mass Spectral Data and Protein Sequence Databases," Anal. Chem., vol. 75, p. 3792-3798, (2003).

Sadygov et al., "Central Limit Theorem as an Approximation for Intensity-Based Scoring Function," Anal. Chem., vol. 78, p. 89-95, (2006).

* cited by examiner

| # | Id# | (M+H)+ | Delta | P | E | Ions | Count | Reference | Peptide |
|---|---|---|---|---|---|---|---|---|---|
| 1. | 0 | 1502.66980 | 0.0000 | 23.796 | 0.628 | 24/28 | 1 | MYG_HORSE | K.HPGDFGADAQGAMTK.A |
| 2. | 0 | 1502.66980 | 0.5203 | 11.414 | 1.000 | 16/28 | 2 | MYG_TUPGL | K.HPGDFGADAQAAMSK.A |
| 3. | 0 | 1501.64940 | 0.6661 | 7.944 | 1.000 | 13/28 | 0 | MYG_CASFI | K.HPGBFGADABGAMNK.A |
| 4. | 0 | 1503.74250 | 0.7674 | 5.534 | 1.000 | 9/20 | 0 | ATS18_HUMA | R.GWFYQWKPYTK.V |
| 5. | 0 | 1502.74660 | 0.8921 | 2.568 | 1.000 | 6/22 | 0 | Y1450_METJ | K.YKNFMLATHYSK.L |
| 6. | 0 | 1501.74732 | 0.8365 | 3.892 | 1.000 | 8/24 | 0 | RS24_METAC | K.GYAKVYADEARMK.Q |
| 7. | 0 | 1503.77421 | 0.7996 | 4.769 | 1.000 | 9/24 | 4 | MURA2_BACH | K.GLGANIWREQMTK.Q |
| 8. | 0 | 1502.70302 | 0.7596 | 5.719 | 1.000 | 10/24 | 0 | AGAL_BACSU | K.TIGLCHSVQVCTK.D |
| 9. | 0 | 502.89149 | 0.7752 | 5.350 | 1.000 | 10/26 | 0 | ATPG_ODOSI | K.ITMAMKLVAAAKVR.R |
| 10. | 0 | 1503.84361 | 0.8239 | 4.191 | 1.000 | 8/22 | 0 | RRPL_DUGBV | K.VDFSNLLKHRFK.L |

1. MYG_HORSE (P68082) Myoglobin
2. MYG_TUPGL (P02165) Myoglobin
3. MYG_CASFI (P14396) Myoglobin
4. ATS18_HUMAN (Q8TE60) ADAMTS-18 precursor (EC 3.4.24.-) (A disintegrin and metalloproteinase
5. Y1450_METJA (Q58845) Hypothetical protein MJ1450
6. RS24_METAC (Q8TJT2) 30S ribosomal protein S24e
7. MURA2_BACHK (Q6HAU9) UDP-N-acetylglucosamine 1-carboxyvinyltransferase 2 (EC 2.5.1.7)
8. AGAL_BACSU (O34645) Alpha-galactosidase (EC 3.2.1.22) (Melibiase)
9. ATPG_ODOSI (Q06908) ATP synthase gamma chain, chloroplast precursor (EC 3.6.3.14)
10. RRPL_DUGBV (Q66431) RNA-directed RNA polymerase (EC 2.7.7.48) (L protein)

Figure 7

EVALUATING THE PROBABILITY THAT MS/MS SPECTRAL DATA MATCHES CANDIDATE SEQUENCE DATA

CROSS-REFERENCE TO RELATED APPLICATIONS

This application claims the benefit of U.S. patent application Ser. No. 11/703,941, filed Feb. 7, 2007, and entitled, "Data Analysis To Provide A Revised Data Set For Use In peptide Sequencing Determination," which is incorporated herein in its entirety.

FIELD OF THE INVENTION

This invention relates generally to methods for processing data derived from mass spectrometric analysis of peptides and proteins, and more specifically to a method of processing mass spectral data generated by fragmentation of product ions using a non-ergodic reaction, such as electron transfer dissociation (ETD), to calculate expectation values representative of the confidence of match to a candidate sequence.

BACKGROUND OF THE INVENTION

Mass spectrometry in conjunction with database searching has become a method of choice for fast and efficient identification of proteins in biological samples. In particular tandem mass spectrometry of peptides in a complex digest can provide information relating to the identity and quantity of the proteins present in the sample mixture. Tandem mass spectrometry achieves this by isolating specific mass-to-charge ratio values (precursor ions) of the peptides, subjecting them to fragmentation and providing product ions that are used to sequence and identify peptides. The information created by the product ions of the peptides can be used to search protein and nucleotide sequence databases to identify the amino acid sequence represented by the spectrum and thus identify the protein from which the peptide was derived.

The identification procedure is performed in high-throughput mode by comparing experimental data such as the mass spectra with characteristic data such as theoretical sequences for peptides of previously identified ("known") proteins. Searchable databases are available, e.g., at the National Center for Biotechnology Information (NCBI). They include databases of nucleotide sequence information and amino acid sequence information of peptides. To identify peptides, database searching programs typically compare each MS/MS spectrum against the sequences contained in the database, and a probability score is assigned to rank the most likely peptide match. The algorithms typically utilize mass-to-charge (m/z) information for identification purposes of the various product ions. The matching of peptide sequences based on their MS/MS fragmentation spectra to data from peptides extracted from databases does not necessarily identify them unambiguously or with 100% confidence. Some spectra may match very closely while others match less closely. A close match may or may not indicate the identity of the unknown peptide. Ranking of matches can be used to identify unreliable matches. For example, a second-best match in one analysis may be a true match indicating identity, whereas the best match in another analysis may be a false match obtained by chance, at random.

The fragmentation of precursor ions can be provided by various methodologies and mechanisms. Ion activation techniques that involve excitation of protonated or multiply protonated peptides include collision-induced dissociation (CID), and infrared multiphoton dissociation (IRMPD), and data generated using such techniques have traditionally been used to identify sequences. The advent of new non-ergodic fragmentation methodologies such as ETD and Electron Capture Dissociation (ECD), have created new capabilities for mass spectrometry. Due to its non-ergodic character, ETD is thought to provide more complete information on primary structure of peptides. At the same time, spectra created via ETD fragmentation are more complicated. In addition to the fragment ions, the spectra contain products of proton abstraction, rearrangement and neutral losses mainly, due to but not limited to, amino bond related groups. In many cases, fragment ions in ETD are less abundant than the charge-reduced forms of the precursor ion. It has been found that the use of algorithms and software that has been written specifically to evaluate spectra produced via CID produces erroneous results if applied to spectra produced via ETD, causing the confidence that one has that a match is correct to be low. All of these problems call for a new algorithmic approach optimized for peptide identification of ETD spectra, other non-ergodic ion-ion reaction produced spectra, and multiple or sequential ion-ion reaction produced spectra.

SUMMARY

In one aspect of the present invention a new database search methodology is provided that provides a probability that spectral data from a non-ergodic reaction via mass spectrometry matches a candidate sequence from a set of sequences in a database by random. The methodology may comprise three parts. The first part pre-processes the spectral data and retains only the most relevant data for the database search. The second part comprises searching a database using the pre-processed spectrum to assign a probability or expectation that the spectrum matches a candidate sequence from a set of sequences in a database by random. The search methodology uses a new probability model, a compound distribution based on the number of product ion mass-to-charge ratios and the number of intensity values that are shared between the product ion spectral data and the sequence database, to accurately predict the probability of the peptide identification being a correct match, and not a random event. The third part modifies the results from the database search of a single spectrum to account for the plurality of spectra in a data set.

In another aspect of the present invention an expectation value is generated, a value that indicates whether the ion spectral data matches a candidate sequence in a sequence database.

In yet a further aspect of the present invention, a storage medium encoded with machine-readable computer program code is provided, the storage medium including instructions for generating a compound probability that production spectral data matches a candidate sequence in a sequence database by random, the product ion spectral data having been generated by a non-ergodic process.

These and other aspects of the invention will become apparent from the following description. In the description, reference is made to the accompanying drawings that form part thereof. The description and figures do not necessarily represent the full scope of the invention and reference is made therefore, to the claims herein for interpreting the scope of the invention.

BRIEF DESCRIPTION OF THE DRAWINGS

Like reference numerals refer to corresponding parts throughout the several views of the drawings.

DETAILED DESCRIPTION OF EMBODIMENTS

Figure 1:
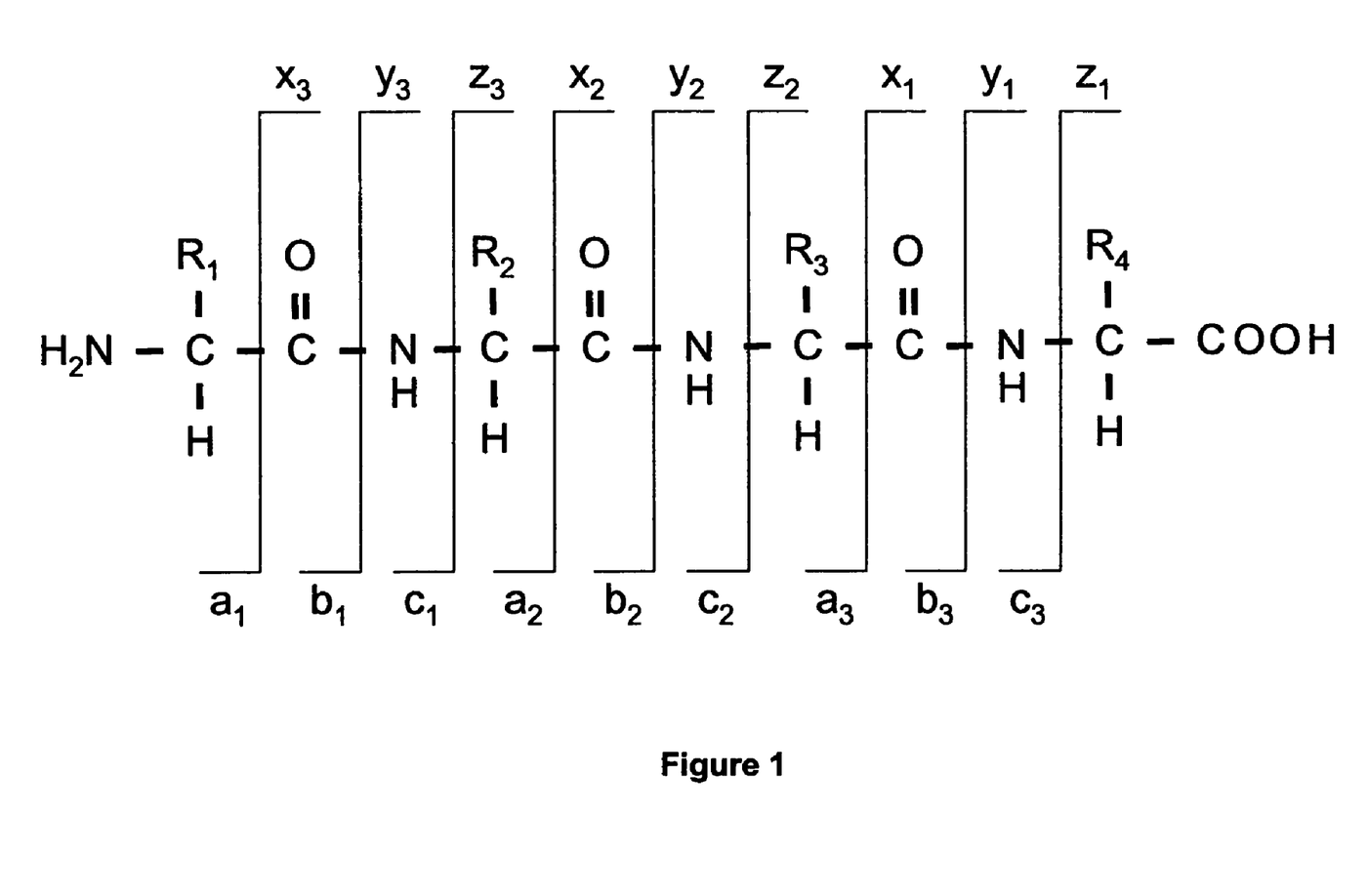
FIG. 1 depicts a nomenclature typically adopted for the fragment of peptides and proteins.

Before describing the invention in detail, a few terms that are used throughout the description are explained. A nomenclature typically adopted (and used herein) for the fragments of peptides and proteins has been suggested in the literature and is depicted in FIG. 1. The three possible cleavage points of the peptide backbone are called a, b and c when the charge is retained at the N-terminal fragment of the peptide and x, y and z when the charge is retained by the C-terminal fragment. The numbering indicates, which bond is cleaved counting from the N- and the C-terminus respectively, and thus also the number of amino acid residues in the fragment ion.

ETD is an ion-ion reaction in which the transfer of a thermal electron is exothermic and causes the peptide backbone to fragment by a non-ergodic process, i.e., a process does not involve intramolecular vibrational energy redistribution. ETD (as well as ECD) occurs on a time scale that is short compared with the internal energy redistribution that occurs in CID, and consequently, most specific fragment forming bond dissociations are typically randomly along the peptide backbone, and not of the side-chains. ETD yields product ions that represent cleavages between most of a peptide's or protein's amino acids. ETD produces mainly c and z* fragment ions (ion products) and to a much smaller extent a*, y ions and z' and c* ions. The ETD reaction generally results in almost complete sequence coverage for small peptide ions, with the exception of dissociation N-terminal of Proline residues, which unlike the case for all other amino acids, requires dissociation of two bonds.

In an ETD experiment, multiply-charged peptide cations are reacted with an electron transfer reagent to initiate the dissociation of the cations yielding sequence specific ion products according to equation (1).

$$[M+nH]^{n+}+A^{-*} \rightarrow [C+(n-m)H]^{(n-m-1)+}+[Z+mH]^{m+}+A \quad (1)$$

where A−* is the electron transfer reagent, the $[M+nH]^{n+}$ is the cation and the $[C+(n-m)H]^{(n-m-1)+}$ and $[Z+mH]^{m+}$ are the c and z* type fragment ions, respectively.

The reaction of the electron transfer anion proceeds through both electron transfer (with and without dissociation) and proton transfer (without dissociation). Electron transfer reactions that proceed with dissociation give rise to cleavage along the peptide backbone, and cleavage of the Cysteine bond (if present). The products of such reactions are referred to as second order ion products.

ETD, therefore, is a process of three competing reactions, one of which yields the desired product ion representing sequence specific information (second order ion products), while the other reaction pathways yield product ions that provide no specific information about the amino acid sequence of proteins or peptides.

However, first order ion products can undergo sequential reactions that lead to higher-order charge reduced ions of the precursor cation and, in extreme cases, to the neutralization of the precursor. In these cases the ion-ion reaction leads to the reduction of charge without any dissociation into first order ion products according to equation (2):

$$[M+nH]^{(n-1)*}+A^{-*} \rightarrow [M+nH]^{(n-2)**}+A \quad (2)$$

Similarly, the successive transfer of a proton from the excited intermediate to the anion reagent can lead to the formation of charge reduced species without dissociation into second order fragment ions according to equation (3):

$$[M+nH]^{(n-1)+}+A^{-*} \rightarrow [M+(n-1)H]^{(n-2)+}+AH \quad 3)$$

The successive reaction of the first order product ion with electron transfer reagent can lead to a number of ion-ion reaction products that can be comprised of a mixture of species formed exclusively by proton transfer or electron transfer reactions or a mixture of both electron and proton transfer reactions. It is to be noted that the exact charge state and compositional nature of these ion products are usually difficult to determine without use of a high resolution mass spectrometer. Unit resolution mass spectrometers can not distinguish between the different isobaric species of the first order ion-ion products resulting from the successive reaction of the first order ion product with electron transfer reagent.

Having explained the meaning of a few terms that have been used in describing the invention, the broad concepts of the invention will now be explained with the aid of FIGS. 2-7.

The invention provides, methods and apparatus, including computer program products, for calculating the confidence of a match between product ion spectral data and a candidate sequence from a sequence database. The invention evaluates the confidence or reliability of a match based on matches of characteristics between the experimental spectral data and the sequence database, characteristics including ion abundance and mass-to-charge ratios.

In one aspect of the invention, there is provided a method for generating a compound probability that product ion spectral data matches a candidate sequence in a sequence database by random, the product ion spectral data having been generated by a non-ergodic process. The method pre-processes the product ion mass spectral data in a manner to infer all information useful for peptide identification, accounts for redundant information and removes it, and cleans the spectral data from ions related to intact peptides. This pre-processed product ion spectral data is then used in a database search for identification process. The identification process is modeled as a random event dependent on the product ion current intensities and product ion peaks in the product ion spectral data, and the collective probabilistic properties of the sequences contained in the sequence database and spectral data set. It is assumed that all matches between the product ion spectral data obtained via the non-ergodic mass spectrometry and the sequence database are by random, and from that one is able to determine which of the matches has the smallest probability of being a random match. In this sense, the type I error of the Null Hypothesis is minimized. The form of the probability mode utilized is a compound distribution of two random variables—the number of mass-to-charge ratio peaks that are shared or held in common between the product ion mass spectral data from mass spectrometry and the sequence database, and the ion intensity values that are shared, or held in common within the product ion spectral data.

A typical system for generating the compound probability that product ion spectral data matches a candidate sequence in a sequence database by random according to one aspect of the invention comprises a general-purpose programmable digital computer system of conventional construction, which can include memory and one or more processors running an analysis program. The computer system has access to a source of data such as product ion spectral data for experimental peptides, the source provided for example by a tandem mass spectrometer capable of performing ETD-MS/MS analysis. A source of mass spectral data can be any mass spectrometer capable of generating product ion spectral data, such as a triple quadrupole, ion trap, time-of-flight, ICR, electrostatic or hybrid mass spectrometer. The source of the product ion spectral data produces product ion mass spectral data for one or more peptides in an experimental sample. The computer system also has access to a single or a collection of peptides databases, such as a publicly-available protein or nucleotide sequence databases. No particular structure or format of the information in the sequence database is required.

Figure 2:
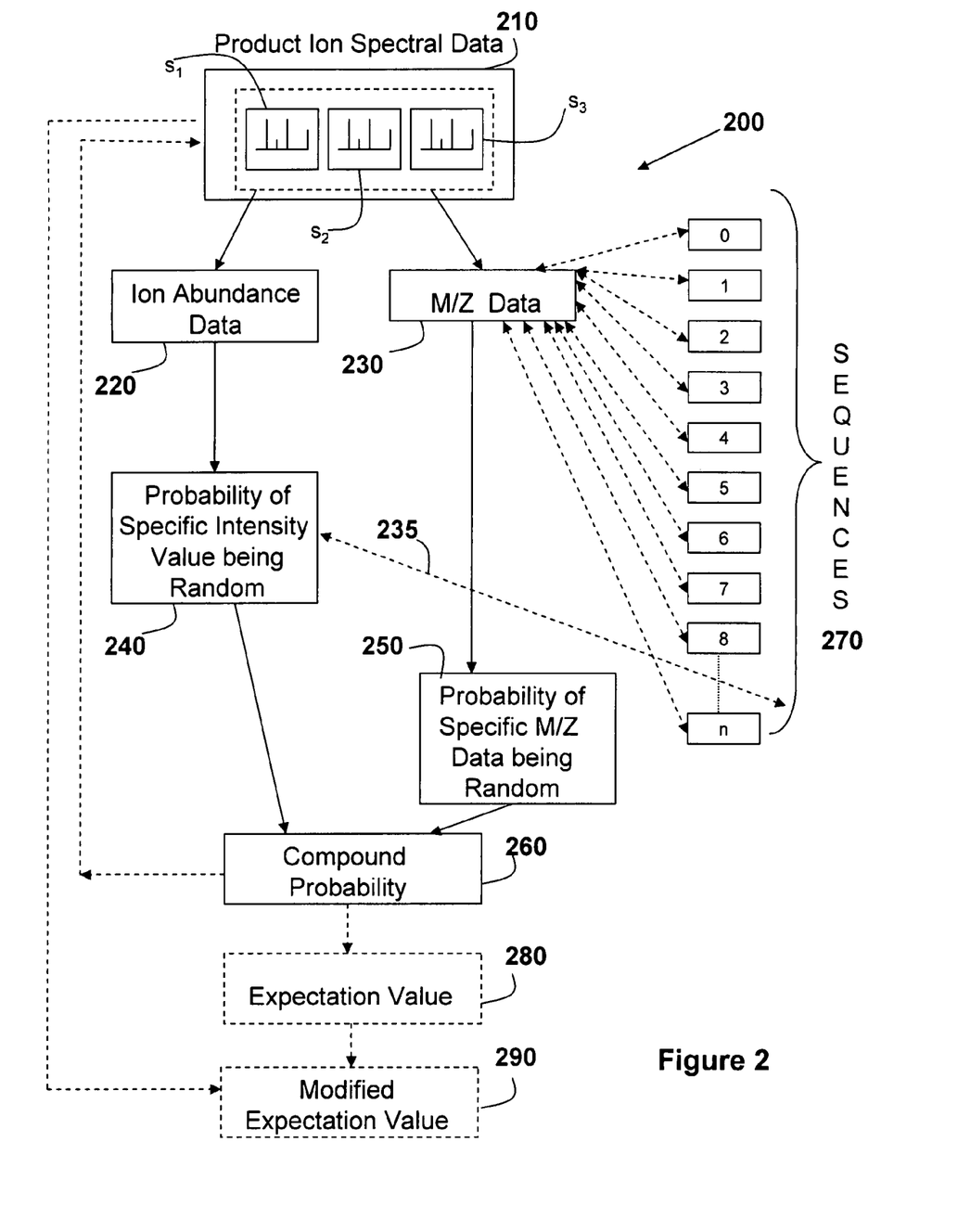
FIG. 2 is a flowchart illustrating the steps that are performed in order to analyze product ion data so that an expectation value can be generated via calculation of a compound probability that product ion spectral data matches a candidate sequence in a sequence database by random and accounts for the plurality of spectra in the data set, in accordance with an aspect of the present invention.

FIG. 2 is a flowchart 200 depicting some of the steps for analyzing product ion data so that a compound probability can be generated that product ion spectral data matches a candidate sequence in a sequence database by random, the product ion spectral data having been generated via tandem mass spectrometry. FIG. 2 also depicts the additional steps required to determine the expectation value that the product ion spectral data matches a candidate sequence in a sequence database.

As shown in FIG. 2, step 210 relies on the fact that ion product data has already been generated, in one aspect of the invention by an ion-ion reaction mechanism or process such as ETD. As illustrated in FIG. 2 the experimental product ion spectral data typically comprises one or more sets of data, the first product ion spectral data identified here as $S_1$, and the additional product ion spectral data identified here as $S_2$ and $S_3$. The experimental datasets $S_1$, $S_2$ and $S_3$ representing data that has been acquired are various stages of the fragmentation process, for example, multiple scans acquired over the time it takes for the ETD process to occur.

In one implementation, the ion product data is analyzed to distinguish "useful" data from not so useful data, which may be performed, for example, by distinguishing data associated with first order product ions from data associated with higher order product ions, as described in co-pending U.S. patent application Ser. No. 11/703,941, which is incorporated herein by reference. The data analysis for this process, in addition to the subsequent analysis that is described below, may be carried out by means of a storage medium encoded with machine-readable computer program code. For example the data analysis may be carried out by a computer system comprising for example a central processing unit (CPU), memory, display and various additional input/output devices. Such a data analysis system may form part of the overall mass analyzer or be a separate stand alone unit, connected to the mass analyzer through input/output interfaces known in the art. Those in the art will also appreciate that the series of computer instructions that embody the functionality described hereinbefore can be written in a number of programming languages for use with many computer architectures and numerous operating systems.

Having acquired the product ion spectral data to be in the form desired, two distinct pieces of information are taken from the product ion spectral data prior to further analysis being undertaken. The first type of information, the ion abundance data 220 is associated with the ion abundance values corresponding to the product ion peaks of the spectral data 210a, 210b or 210c. The second type of information, the m/z data 230, is associated with the mass-to-charge ratio values of the product ion peaks of the spectral data 210a, 210b or 210c. Each of the types of information is subsequently processed independently of one another, and a probability distribution for each is determined. From the ion abundance data 220, a first probability, the probability of a specific intensity value being generated at random is determined in step 240, and from the M/Z data 230, a second probability, the probability of a specific M/Z value being generated at random is determined in step 250.

As part of step 240, the number of intensity matches between the product ion spectral data and the sequences in the sequence database can be used in step 235 to generate a conditional probability in step 240. As part of step 250, the generated m/z values are compared against product ions of one or more known or sequences (0 to n), commonly referred to as candidate sequences from a database 270. The two probability values are then combined to generate a compound probability in step 260 that the experimental ion product spectral data matches data (0 through n) in the sequence database(s) 270 at random. From this compound probability 260, an expectation value can be determined (in step 280), the expectation value being the probability that the experimental ion product spectral data matches a candidate sequence in the sequence database. This expectation value can be adjusted in step 290 to compensate for multiple-testing, that is to compensate for the experiment being carried out a multiple of times (due to the plurality of spectral data), generating multiple test results, and accounting for the size of the spectral data set.

As mentioned previously, the second probability is determined independent of the first probability. Since each probability has a confidence level associated with it, the confidence level associated with the first probability not necessarily being the same as the confidence level associated with the second probability, the confidence level value associated with the compound probability is therefore better than either a confidence level value associated with the first probability or a confidence level value associated with the second probability.

Figure 3:
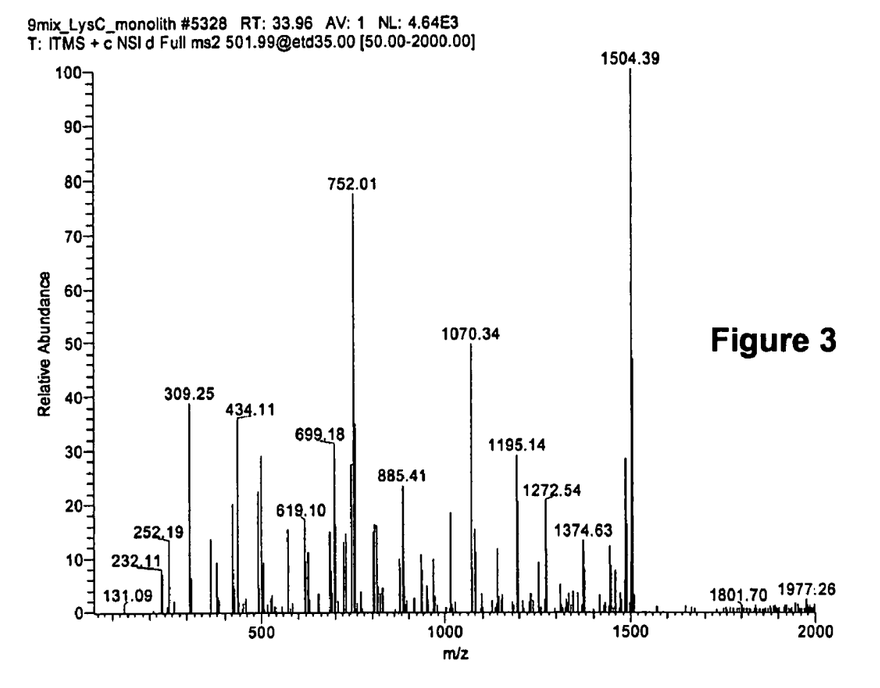
FIG. 3 illustrates original experimental product ion spectral data.

The approach taken by the present invention is explained below in an example of a spectrum of horse myoglobin peptide. As indicated earlier, typically, the product ion spectral data contains a vast quantity of information, only some of which is considered useful from the point of view sequence identification. FIG. 3 shows sample experimental mass-to-charge ratio spectral data obtained after fragmentation by ETD of the horse myoglobin peptide, "HPGDFGADAQ-GAMTK". The spectrum shows characteristic features of the ETD spectra, including but not limited to charge reduced precursors, electron transfer products, anion adducts, side chain losses, hydrogen transfer products, fragment ions, products or fragment ion adducts and products of fragment ion neutral losses. Therefore, the spectral data representative of the fragments contains not only first order ion products which have come directly from the fragmentation of the intact and charged precursor, but second order ion products which are the results of fragmentation of the first order ion products. Thus in this particular example, the reduced charge ions of the intact precursor dominate the spectrum (peaks at 752 Th and 1504 Th, +2 and +1 species of the intact precursor, respectively). There are also a large number of peaks in the spectrum that correspond to the neutral losses, hydrogen rearrangements and other reactions that do not carry applicable information for primary structure determination.

Figure 4:
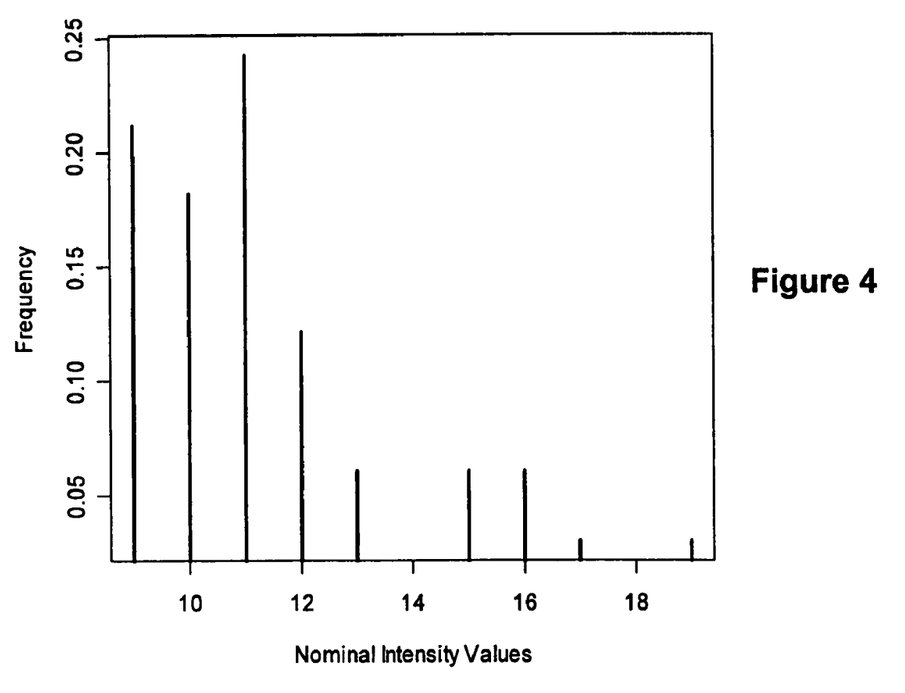
FIG. 4 illustrates pre-processed experimental product ion spectral data, according to an aspect of the present invention.

The first step of the invention step is to take the spectrum illustrated in FIG. 3, the first product ion spectral data, and to "clean" or pre-process the spectrum in preparation for further analysis and database searching. This step essentially generates product ion data in the form required to identify the more "useful" data that can be used in the analysis process, and at the same time typically significantly simplifies the product ion spectral data. One form of the pre-processed product ion spectral data is illustrated in FIG. 4 which shows on the horizontal axis (as viewed by the reader) the nominal intensity values of the m/z product ion spectral peaks, and then indicate the frequency at which those intensities appear on the vertical axis (once again as viewed by the reader). Acquisition of this information is considered to form part of step 220, in which ion abundance values are determined.

Having acquired the ion abundance values, one is then able to utilize that information to determine an intensity probability distribution, the intensity probability distribution representing a first probability that the product ion spectral data was generated at random. In one aspect of the invention, this can be achieved by considering the intensity probability distribution to be a conditional distribution, P(I|C), a distribution of the shared intensity under the condition of the shared peak count, and is calculated using p-value from the self-convolution of the experimental spectrum. Hence the intensity probability distribution can be represented as $$P(I|C) = P((S*S)^C, x > I)$$

where S denotes the experimental product ion spectrum data, $(S*S)^C$ denotes the Cth order self-convolution of the spectrum, $P((S*S)^C, x > I)$ is the probability of observing the same shared intensity or higher in the Cth order self-convolution spectrum, and I is the nominal intensity. This particular form for determination of the intensity probability distribution is based on modeling, but it will be apparent to those skilled in the art that other forms of determination can be used.

Figure 5:
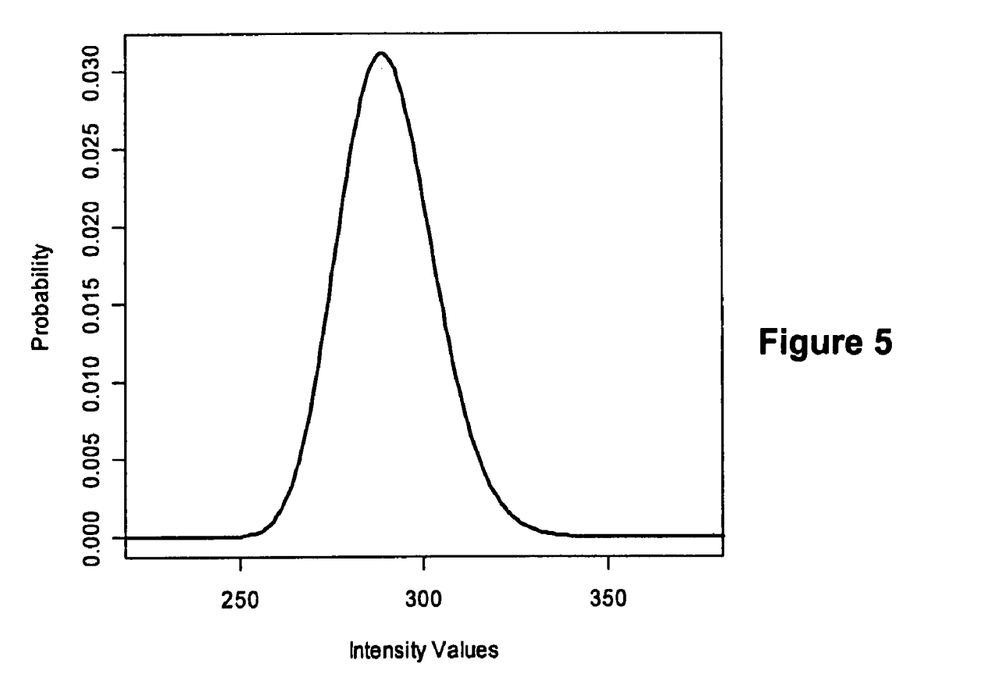
FIG. 5 illustrates a 24-fold self-convolution of the spectrum illustrated in FIG. 4.

FIG. 5 shows the probability distribution, P(I|C), of the experimental spectrum from the horse myoglobin peptide, "HPGDFGADAQGAMTK" mentioned above. The highest frequency of common nominal intensity value, the shared peak count (or the highest number of matches) between the experimental product ion spectral data and the sequence database is 24. The 24-fold self-convolution of the spectrum with itself is shown in FIG. 5. The conditional probability values are calculated from this distribution as p-values. For example, the nominal amount of the shared peak intensity explained by the horse peptide in this spectrum is 286. To calculate the probability of this intensity probability happening by random, the p-value is calculated from the above distribution with ordinate value of 286, which in this case is 0.628.

Figure 6:
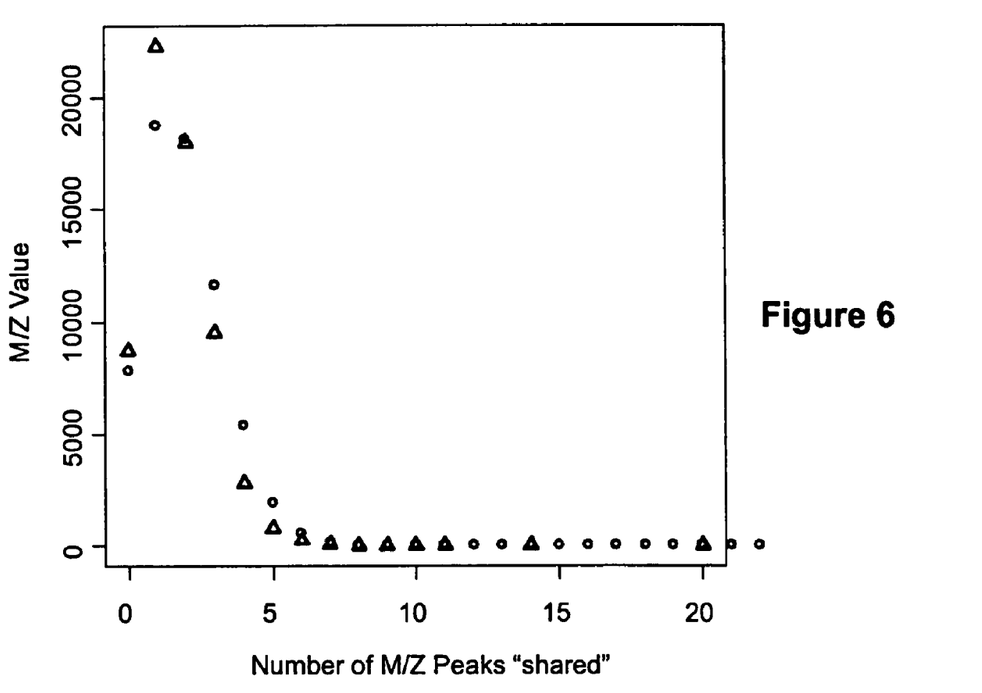
FIG. 6 illustrates the number of mass-to-charge ratio matches, obtained by model and experiment, from the sequence database to the product ion spectral data.

Having acquired the mass-to-charge ratio values, one is then able to utilize that information to determine a fragment probability distribution, the fragment probability distribution representing a second probability that the product ion spectral data was generated at random. In one aspect of the invention the fragment probability distribution of the shared mass-to-charge ratio peak counts P(C) is assumed to have a Hypergeometric distribution:

$$P(C) = P_{K,N}(K_1, N_1) = \frac{C_K^{K_1} * C_{N-K}^{N_1-K_1}}{C_N^{N_1}}$$

where N is the number of all fragments (product ions) in the sequence database, K is the number of product ions represented in the sequence database that match the mass-to-charge ratio values of the product ions spectral data, $N_1$ is the number of product ions in the first product ion spectral data, and $K_1$ is the number of product ions in the database that match the mass-to-charge ratio of the product ion spectral data. The distribution is known to accurately describe a peptide match to a tandem mass spectrum with a high specificity.

For this particular example, the number of mass-to-charge ratio matches from the sequence database to the product ion spectral data is presented in the FIG. 6. FIG. 6 illustrates the results from more than one product ion spectrum (210a, 210b, 210c for example), illustrating on the horizontal axis (as viewed by the reader) the number of M/Z peaks that are "shared" between the product ion spectral data and the sequence database, and the vertical axis (once again as viewed by the reader) the M/Z value. The triangles in the figure represent the observed peak values from the experimental product ion spectral data, and the circles represent the theoretical peak values from the sequence database (270). As seen in FIG. 6, there is substantial agreement between the observed and predicted/theoretical distributions. The probabilities, P(C), are calculated using this distribution. For every peptide this probability is calculated based on its length and the number of product ion matches.

As described above, the present invention is based on a random probability model for peptide identification scores from the sequence databases. Thus it is assumed that the probability model is governed by a compound distribution:

$$P(CI) = P(I|C) * P(C)$$

where P(CI) is the compound distribution of the spectrum match to an amino acid sequence from a database, where C is the shared or common mass-to-charge ratio count, and I is the shared or common peak abundance.

Figure 7:
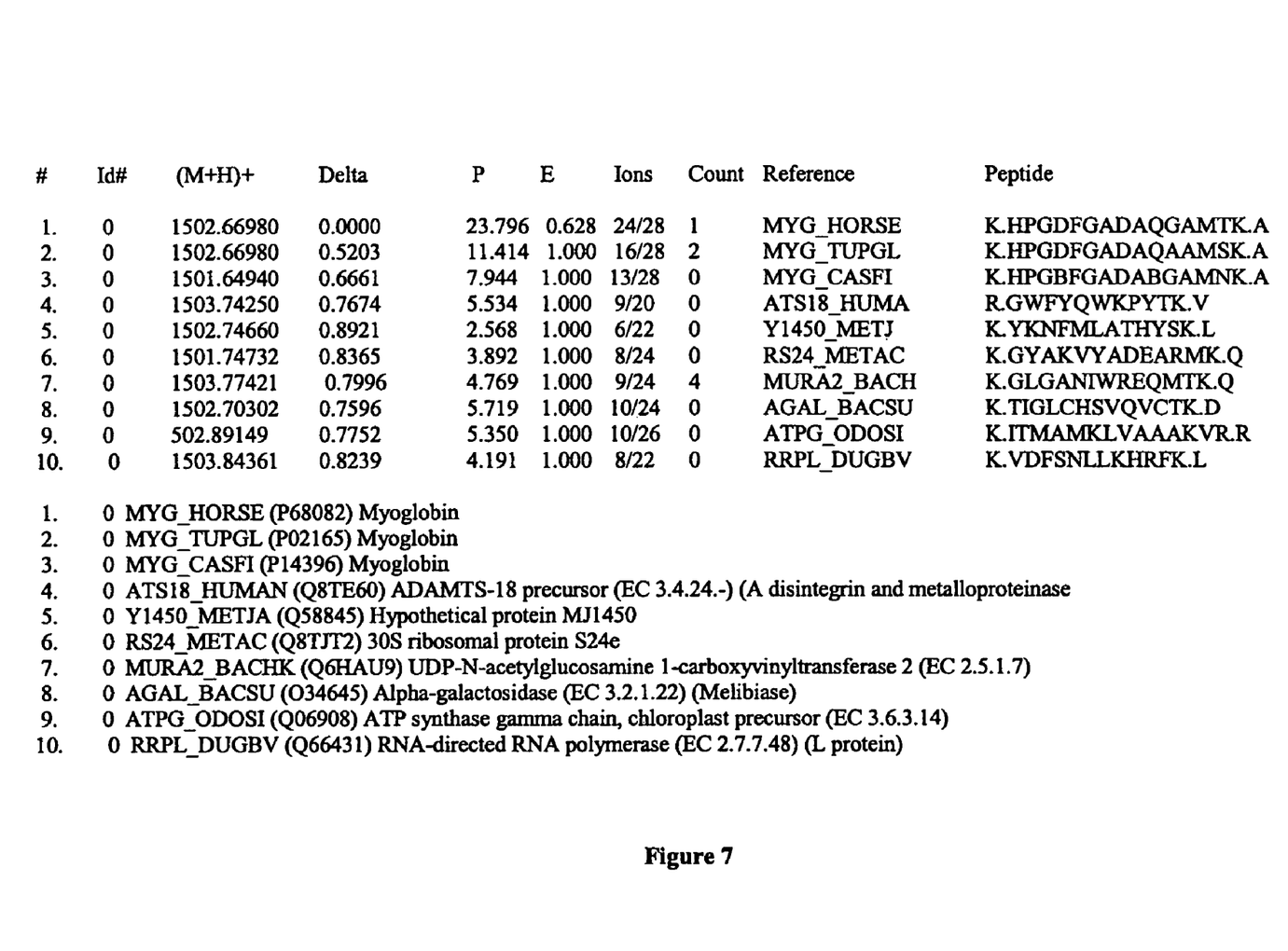
FIG. 7 illustrates an output generated by utilizing the methodology of the present invention.

The final probability is calculated using P(C) and P(I|C). The final score for the horse myoglobin peptide is 23.8, a highly confident score, as shown in FIG. 7.

From these distributions an expectation value, a probability that the random match with the same probability would occur due to repetitive trials in the database, is generated (step 280). The expectation value, a value that quantifies how closely the ion spectral data matches a candidate sequence in the database, at first is calculated for database specific variation using only the number of the candidate peptides in the database.

In one aspect of the invention, the expectation, Exp, can be represented as:

$$Exp = L * (1 - (1 - P(x > X_{extreme}))^L)$$

where, L is the number of peptide candidates from the database, $X_{extreme}$ is the peptide score (for the horse myoglobin example it is 23.8), and $P(x > X_{extreme})$ is the cumulative probability of the scores better than 23.8.

This expectation value can be further modified or adjusted (step 290) to account for the number of product ion spectral data sets (a, b and c) acquired in step 210, a multiple testing problem. In one aspect of the invention, a Benjamini-Hochberg procedure is used to account for the size of the product ion spectral data set (210).

After the all searches are finished the expectation is modified to account for the number of spectra in the database, a multiple testing problem. An example of the output generated by utilizing the methodology of the present invention is shown in FIG. 7. The output provides information, for each candidate sequence, on the shared/common mass-to-charge ratios, on the probability of a match and the expectation value which is a combined or modified expectation value accounting for sequence database size and the number of product ion spectra acquired, as well as protein origin and other characteristic information. This modification can be based on pre-processed or original spectral data.

Aspects of the invention can be implemented in digital electronic circuitry, or in computer hardware, firmware, software, or in combinations of them. Some or all aspects of the invention can be implemented as a computer program product, i.e., a computer program tangibly embodied in an information carrier, e.g. in a machine-readable storage device or in a propagated signal, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers on one site or distributed across multiple sites and interconnected by a communication network.

Some or all of the method steps of the invention can be performed by one or more programmable processors executing a computer program to perform functions of the invention by operating on input data and generating output. Method steps can also be performed by, and apparatus of the invention can be implemented as, special purpose logic circuitry, e.g., an FPGA (field programmable gate array) or an ASIC (application-specific integrated circuit). The methods of the invention can be implemented as a combination of steps performed automatically, under computer control, and steps performed manually by a human user, such as a scientist.

Although various aspects of the invention have been disclosed, it should be apparent to those skilled in the art that various changes and modifications can be made without departing from the scope of the present invention, and incorporating some, if not all the advantages discussed above. For example, other non-ergodic ion-ion reactions can be utilized, including multiple or sequential ion-ion reactions. These and other modifications are intended to be within the scope of the present invention. Accordingly, other modifications are within the scope of the following claims:

What is claimed is:

1. A method for generating a compound probability that product ion spectral data matches a candidate sequence in a sequence database by random, the product ion spectral data having been generated by a non-ergodic process as implemented in a mass spectrometer instrument, comprising:

(a) generating a first product ion spectral data from one or more biological samples using the mass spectrometer instrument; wherein the steps following steps are preformed by a computer;

(b) preprocessing the first product ion spectral data;

(c) determining product ion abundance values and product ion mass-to-charge ratio values for each of a plurality of peaks from the pre-processed first product ion spectral data;

(d) utilizing the product ion abundance values to determine an intensity probability distribution, the intensity probability distribution representing a first probability that the product ion spectral data was generated at random;

(e) utilizing the mass-to-charge ratio values of the product ions to determine a fragment probability distribution, the fragment probability distribution representing a second probability that the product ion spectral data was generated at random;

(f) determining the compound probability based on the intensity probability distribution and the fragment probability distribution, the probability representing a probability that the generated product ion spectral data matches a candidate sequence in the sequence database at random; and (g) displaying to a user, the candidate sequence which best matches the generated first product ion spectral data based on the determined compound probability.

2. The method of claim 1, wherein the first probability is determined independent of the second probability, and a confidence level value associated with the compound probability is better than either a confidence level value associated with the first probability or a confidence level value associated with the second probability.

3. The method of claim 1, wherein the expectation of compound probability is modified by utilizing additional product ion spectral data.

4. The method of claim 3, wherein the first product ion spectral data comprises data from a first scan, and the additional product ion spectral data comprises data from additional scans.

5. The method of claim 1, wherein preprocessing comprises identifying the product ions from the spectral data that are second and higher order product ions.

6. The method of claim 1, wherein the non-ergodic process comprises ETD.

7. The method of claim 1, wherein the non-ergodice process comprises multiple or sequential ion-ion reactions.

8. The method of claim 1, wherein the intensity probability distribution is determined in part by determining a P-value.

9. The method of claim 8, wherein the P-value is determined from self-convolution of the spectral intensity distribution.

10. The method of claim 1, wherein the fragment probability is determined by comparing the mass-to-charge ratios of one or more of the product ions to one or more known or predicted mass spectra from candidate sequences in a database.

11. The method of claim 1, wherein the fragment probability distribution is determined in part by correlating how many product ions peaks in the product ion spectral data match the peaks in the hypothetical mass spectra from candidate sequences in a database.

12. The method of claim 1, wherein the fragment probability distribution is determined in part by a hypergeometric distribution of the fragment probabilities.

13. The method of claim 1, wherein the fragment probability distribution is determined in part by determining a P-value.

14. The method of claim 1, wherein the compound probability is determined as a compound distribution in the form:

$$P(CI)=P(I/C)*P(C);$$

where P(CI) is the compound probability that product ion spectral data matches a candidate sequence in the sequence database by random, P(I/C) is a conditional intensity probability distribution, and P(C) is the fragment probability distribution.

15. The method of claim 14, wherein P(C) is a probability of the form:

$$P(C) = P_{K,N}(K_1, N_1) = \frac{C_K^{K_1} * C_{N-K}^{N_1-K_1}}{C_N^{N_1}}$$

where N is the number of product ions represented in the sequence database, K is the number of product ions represented in the sequence database that match the mass-to-charge ratio values of the product ion spectral data, $N_1$ is the number of product ions of a candidate sequence, and $K_1$ is the number of the candidate sequence product ions in the database that match the mass-to-charge ratios in the first product ion spectral data.

16. The method of claim 14, wherein P(I/C) is a probability of the form:

$$P(I|C)=P((S*S)^C, x>I)$$

where S is the first product ion spectral data, $(S*S)^C$ is the $C^{th}$ order self-convolution of the first product ion spectral data, and $P((S*S)^C, x>I)$ is the probability of observing the same ion abundance value or higher in the $C^{th}$ order self-convolution of the first product ion spectral data, and I is the nominal intensity.

17. The method of claim 1, further comprising determining the expectation value that the ion spectral data matches a candidate sequence in a sequence database.

18. The method of claim 17, wherein the expectation value for the first product ion spectral data is of the form:

$$Exp=L*(1-(1-P(x>X_{extreme}))^L)$$

where Exp is the expectation value, L is the number of candidate sequences from the sequence database, and $X_{extreme}$ is the compound probability, and $P(x>X_{extreme})$ is the cumulative probability based on the compound probability being greater than compound probability, calculated for the candidate sequence.

19. The method of claim 18, wherein the expectation value is modified by accounting for multiple tests on the spectral dataset.

20. A computer program code stored in a computer readable medium for generating a compound probability that product ion spectral data matches a candidate sequence in a sequence database by random, the product ion spectral data having been generated by a non-ergodic process, the storage medium including instructions for:

(a) acquiring first product ion spectral data;
(b) preprocessing the first product ion spectral data;
(c) determining product ion abundance values and product ion mass-to-charge ratio values for each of a plurality of peaks from the pre-processed first product ion spectral data;
(d) utilizing the product ion abundance values to determine an intensity probability distribution, the intensity probability distribution representing a first probability that the product ion spectral data was generated at random;
(e) utilizing the mass-to-charge ratio values of the product ions to determine a fragment probability distribution, the fragment probability distribution representing a second probability that the product ion spectral data was generated at random; and
(f) determining the compound probability based on the intensity probability distribution and the fragment probability distribution, the probability representing a probability that the generated product ion spectral data matches a candidate sequence in the sequence database by random; and determining an expectation value that the ion spectral data matches a candidate sequence in the sequence database.

* * * * *

UNITED STATES PATENT AND TRADEMARK OFFICE
CERTIFICATE OF CORRECTION

PATENT NO. : 7,555,393 B2
APPLICATION NO. : 11/809703
DATED : June 30, 2009
INVENTOR(S) : Sadygov et al.

Page 1 of 1

It is certified that error appears in the above-identified patent and that said Letters Patent is hereby corrected as shown below:

Claim 1, column 9, line 65/66:
replace "wherein the steps following steps are performed by a computer"
with --wherein the following steps are performed by a computer--

Signed and Sealed this

Ninth Day of February, 2010

David J. Kappos
*Director of the United States Patent and Trademark Office*